United States Patent [19]

Fiore

[11] Patent Number: 5,792,114
[45] Date of Patent: Aug. 11, 1998

[54] INTRODUCER FOR STERILE INSERTION OF CATHETER

[76] Inventor: John M. Fiore, 53 Moonlawn Rd., Troy, N.Y. 12180

[21] Appl. No.: 766,988

[22] Filed: Dec. 16, 1996

[51] Int. Cl.⁶ ................................................ A61M 25/01
[52] U.S. Cl. ........................... 604/171; 604/172; 604/271
[58] Field of Search ............................ 604/54, 171, 172, 604/174, 175, 192, 198, 264, 271, 349

[56] References Cited

U.S. PATENT DOCUMENTS

| | | | |
|---|---|---|---|
| 3,421,509 | 1/1969 | Fiore | 128/239 |
| 3,894,540 | 7/1975 | Bonner, Jr. | 604/171 |
| 4,043,345 | 8/1977 | Kramann et al. | 604/271 |
| 4,652,259 | 3/1987 | O'Neil | 604/171 X |
| 4,957,485 | 9/1990 | Anderson et al. | 604/171 X |
| 5,531,717 | 7/1996 | Roberto et al. | 604/171 X |
| 5,582,599 | 12/1996 | Daneshar | 604/171 X |

*Primary Examiner*—Corrine M. McDermott
*Attorney, Agent, or Firm*—F. T. Morelle

[57] ABSTRACT

A sterile envelope-dispensing catheter introducer. A tubular introducer, through which a catheter is passed, dispenses a membranous shroud, or envelope, from within and out a distal opening thereof. The shroud is withdrawn by manipulation or by the urging of a body organ pressing against a shroud entrainment device. Interposition of the convolutionally rearward transported shroud over (and between) the introducer's distal portion (and the body internal organ surfaces) assures a sterile catheter passage through the introducer and into the organ.

15 Claims, 2 Drawing Sheets

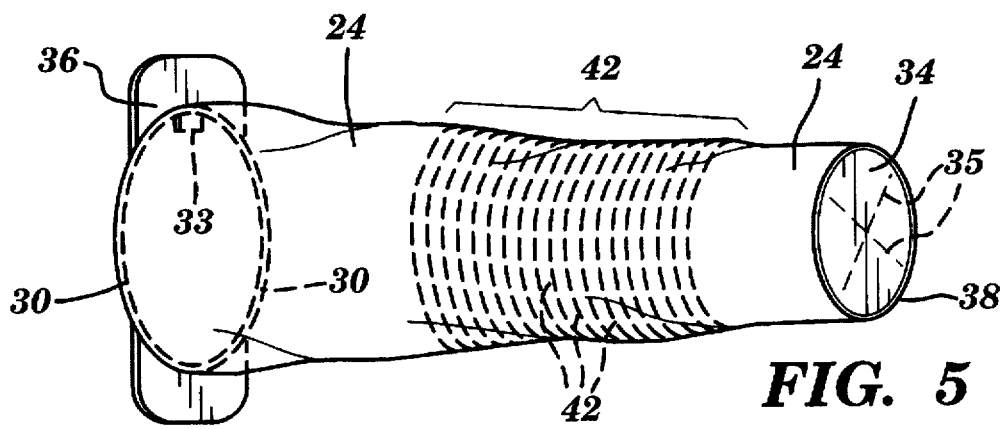
FIG. 5
FIG. 6
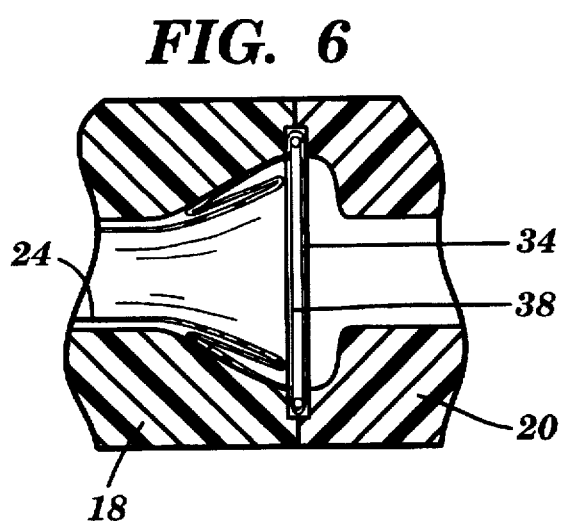
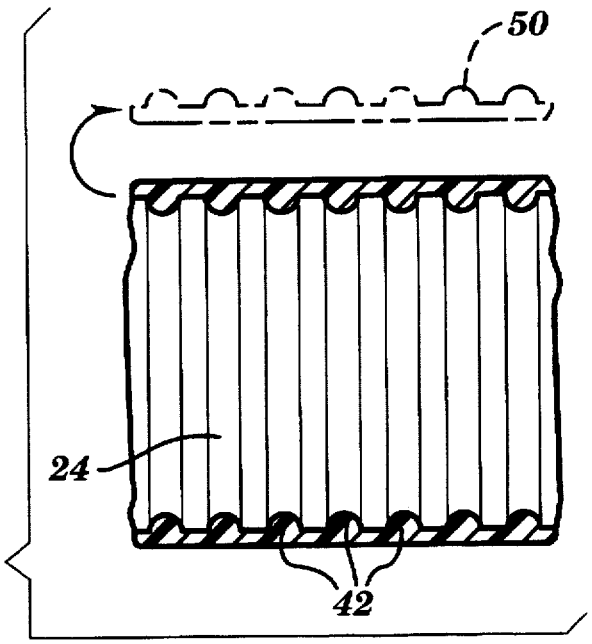
FIG. 8
FIG. 7
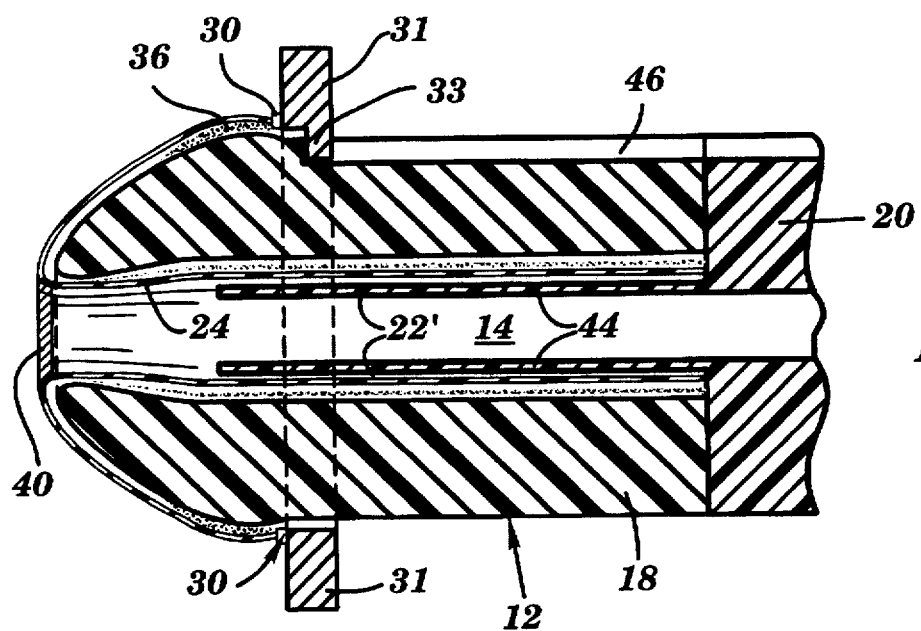

INTRODUCER FOR STERILE INSERTION OF CATHETER

BACKGROUND OF THE INVENTION

1. Field of the Invention

This invention relates generally to delivery apparatus and articles that facilitate the use of devices which by their nature must be properly inserted, deployed or otherwise disposed into a specific situs. In particular, it embodies an instrument that conducts another body, a catheter, into a body orifice while insulating it from contamination that is indigenous to the orifice or its conduit.

2. Relevant Art

Catheters and the medical procedures for their usage are quite well-known in the medical arts. Standard practice, in the use of a catheter, requires a sterile environment encompassing the instruments and the area/orfice of the body being catheterized. Insofar as instruments, skin of the patient and the practitioner and operating area are concerned, sterility can be achieved by modern antisepsis. However, because the catheter of instant concern is to be placed into a body orifice such as, in this particular case, the urethra (male or female), extraordinary care must be taken because the lower urethra and proximal orifice (with respect to the practitionier), although flushed frequently with urine, is nonetheless susceptible of bacterial intrusion. This phenomenon is recognized in the field and many patents are secured by those seeking, as do I, to overcome the spread of such bacterial contamination, or any other, through the urethra and into the bladder, as a catheter is urged thereinto. Two of these patents, U.S. Pat. No. 4,652,259 (O'Neil) and U.S. Pat. No. 3,421,509 (Fiore), are most relevant to my disclosure because they address the presence of a contamination zone/colony in the female and male urethras, respectively; and because they show apparata for which they proclaim a capability for assisting an almost steril insertion of a catheter.

In the O'Neil patent, a urinary catheter assembly, having a catheter tube disposed within an outer sheath, that includes a closure member over the sheath's distal end, is limited in its (initial) penetration of the urethra by a stop member that is fixedly disposed outwardly of the sheath at a specific distance from its distal end. The thesis of the patent is that once inserted to the specific distance, the distal end, which is frangible, is beyond the contamination area/colony and advancement of the sheath, breaking through the distal end, presents a sterile pathway through which the catheter may pass. The patent states that "the problem of bacteria 3 being carried along the urethra 2 is obviated or mitigated" and ". . . initial insertion bacteria are not transferred to the outer tube 6 to any significant degree as it extends through the cover 7 . . . " (emphasis added). Thus any reservations that may arise in the mind of any practitioner are clearly given in the text of the patent. That any bacteria may be carried upstream by a catheter poses a limitation on, and liability for, the use of such a catheter assembly which should be remedied as soon as practicable.

According to the Fiore patent, there is provided and shown a short, separable protective liner assembly which is insertable into the outer extremity of the urethra. The assembly includes, internally, a flexible cover which is extruded through a distal opening thereof when obturated by a catheter extended therethrough. The catheter obturates, in effect, both the tubular assembly and the essentially tubular cover, extending the latter deeper into the urethra, before penetrating past the cover's distal end. Supposedly, contamination is isolated between the cover (tubular) and urethral walls. However, there is presented in the preferred embodiment, a first radially dispensed cover or barrier that is recessed in the assembly distal end. This recess will gather bacteria-contaminated mucosa as the assembly is inserted past the area of contamination. Futher, as the cover (recessed) is forced open by the obturating instrument, the mucosal or lubricant frontal wave—similar to a fluid shock wave—will precede the (catheter) instrument, most likely contaminating its distal end and perhaps its distal orifice(s). Secondary tubular covers, also suggested by this patent, appear to suffer the same limitations or functional obstacles. The principal cause of deficiency in over-laying the bacterial area/colony is that, whatever device is inserted (tube, catheter, introducer, etc.), contaminated body fluid is "pushed" before it; and if an overlay or tubular flexible cover/envelope is used, its convolving deployment "rolls" the cataminated fluid before it. Only a new approach to the deployment of flexible covers, envelopes, sheaths, frangibles, etc. will obviate the aforesaid deficiencies.

INCORPORATION BY REFERENCE

Because they set forth foundational concepts for antiseptic catheter introduction mechanisms, define the paramount medical concerns and disclose procedural usage of catheters and introduction assemblies, U.S. Pat. Nos. 4,652,259 (hereafter '259) and 3,421,509 (hereafter '509) are hereby incorporated by reference, in their entireties.

DEFINITIONS

Since reference will be had to the patents incorporated herein, and I shall set forth new and distinct apparatus and operational modalities, it is incumbent to define terms, both shared and different, of these three works:

"collar" means an encircling or girdling element that may be either continuous or continual and have projections;

"detent" is a small projection (or catch) from off the surface of an element;

"distal(ly)" generally means distant with respect to a practitioner;

"envelope" is a sleeve-like device, a covering herein of an essentially tubular shape having open or closed ends;

"hem" is a border or periphery of a fabric or membrane, herein usually associated with envelope, covering, etc.;

"introducer" means a device that facilitates entry of a body, device or instrument into an orifice of a subject;

"practitioner" means, as opposed to a subject, one using the instant invention on a subject;

"shroud" means an enveloping fabric or membrane, also termed envelope or sleeve; and "sleeve" has its conventional meaning (ibid.).

SUMMARY OF THE INVENTION

I have devised an apparatus and methodology for its use that have overcome the limitations of the relevant art in that my invention exemplifies new (urinary) catheter introducer articles and user techniques that allow a dynamic and complete overlayment of an introducer's distal portion by a membranous shroud as the introducer is inserted into a body conduit. Final disposition of the shroud is between the distal end and a contaminating bacterial colony within the conduit (urethra) of such final disposition. My introducer is a tube-like (lumened and elongated) article having openings at each end and long enough for its distal portion to be inserted into the urethra beyond, and isolating, a zone of contamination. Disposed, by several manufacturing techniques, in the interior (lumen) of the article is a shroud which is to serve as an envelope to cover the inserted portion of the tubular article. The shroud has, in addition to a covering function, additional optional (manufacturer's choice) features such as mucous (-engaging) tractional ribbing or diaphamanous adaptation(s). The shroud is partially deployed out the distal opening of the article and engaged at its hem by a collar device which serves to rigidify somewhat the shroud material. The collar circumscribes the article and is translatable from the distal portion of the article to the proximal in a manner unseen in the art. Tranlation of the collar, by mere manipulation, or by the body part (supporting the urethral orifice) pressing against collar extensions (tabs or lobes), causes an extraction of the shroud from within the article as the article distal end progresses into the urethra. The concommitant regressive movement of the article-enveloping shroud, as the article progresses into the bodily conduit, serves to entrain any contaminant (mucosa/bacteria) encountered and render it stationary, relative to the conduit walls. Other devices/adjuncts to my invention will be introduced here, after a description of the drawings.

BRIEF DESCRIPTION OF THE DRAWINGS

Of the drawings:

FIG. 5 is an illustration of the shroud;

FIG. 6 is another shroud vault detail;

FIG. 7 is a larger sectional view of the distal portion including an alternate shroud stowage; and FIG. 8 is a sectional view of the shroud taken at 8-8 of FIG. 5.

DETAILED DESCRIPTION OF THE PREFERRED EMBODIMENT

Fabrication of catheter introducers, being quite common in the field of medical apparatus and delivery systems, need not be addressed herein as to size and materials. Locations of infection or contamination to be avoided are suitably defined in the two incorporated references and are acknowledged insofar as explanation of my invention requires.

Figure 1:
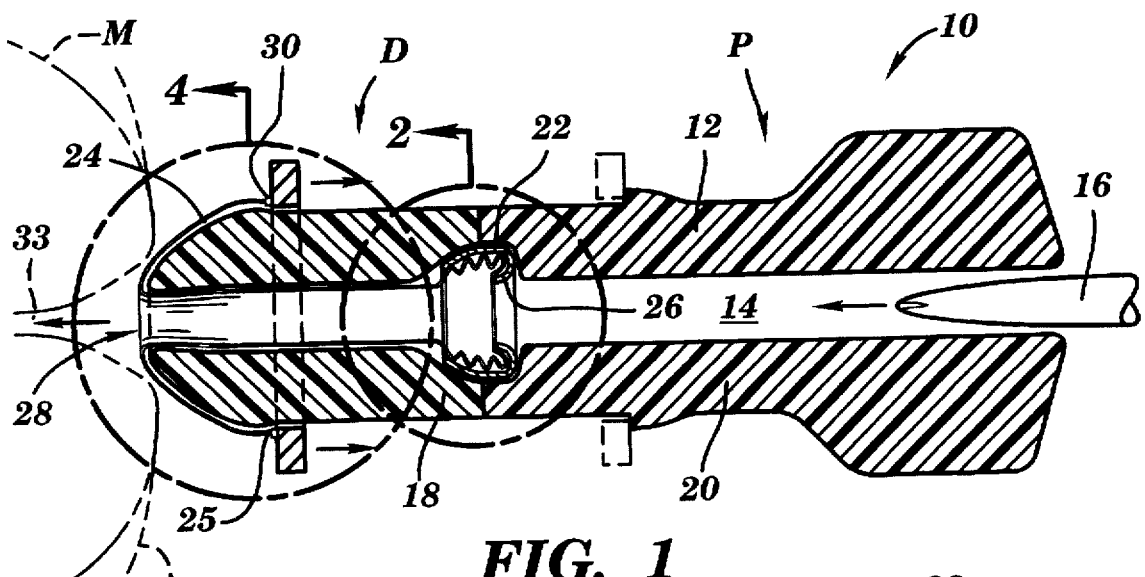
FIG. 1 is a sectional illustration of my invention.

Referring now to FIG. 1, the invention 10 is defined by an essentially tubular body 12 having a conductive lumen or passage 14 therethrough which is receptive of a catheter 16, here of the urethra/bladder class. The body 12 is separable into distal 18 and proximal 20 portions, not necessarily for manufacturing purposes, but rather for elucidation or pedagogic reasons. Those skilled in manufacture of the aforesaid systems may realize the invention in different modalities consistent with my teaching and distinctive improvements to the art. The first noteworthy distinction is a chamber 22 disposed coaxially with the passage 14, but of slightly greater diameter. This chamber, the purpose of which is to act as a repository/vault for a membranous, tubular shroud 24, need not be of any particular size or shape since its geometry is predicated more on size, length and stowability of the shroud 24, alternately termed an envelope. In the preferred embodiment, the chamber 22 is shaped to receive a partially open, hollow annulus/toroid called a holder 26; which holder secures an end of the shroud 24. The other end of the shroud 24 is passed out of the distal opening 28 and drawn convolutionally over the distal portion 18 in an enveloping fashion. In FIG. 1, the hem 25 of the shroud 24 is secured peripherally to an annular collar 30 which is new in this form of apparatus in that is is constructed to translate from a first position D (distal) to a second position P (proximal) and, in doing so, draw the shroud 24 out of passage 14. Thus, it may be seen, that as the distal tip of the invention 10 body is inserted into the urethral orifice 32 of the male M or female F organ, the extreme shoulder of the orifice will press against the collar 30 and urge it proximally toward position P as the distal orifice 28 moves in relatively the opposite direction into the urethra 33. The proximal translation of the shroud hem 25, cojoined to the collar 30, extracts the shroud concommitantly with movement of the distal portion 18 into the urethra 33, thus ensuring that: (1) liquid matter being presented at the distal opening 28 is urged radially away therefrom; and, (2) urethral walls are "carpeted" by the shroud 24. Every portion of the shroud that is extracted toward the proximal position P remains relatively static with respect to the uretral walls because the relatively opposite motion of the distal portion 18. This "carpeting" of urethral walls assures presence of a contaminant-impervious barrier between the urethral situs of contamination and the inserter's distal portion that is disposed within the urethra. Extraction of the shroud is caused by physical motion of its hem, which is retrograde with respect to inserter deposition, making the concept herein presented applicable to other introduction mechanisms. Once the introducer is deposited, the catheter 16 may be introduced with other features of my invention becoming operatively apparent as disclosed in the remaining drawings.

Figure 2:
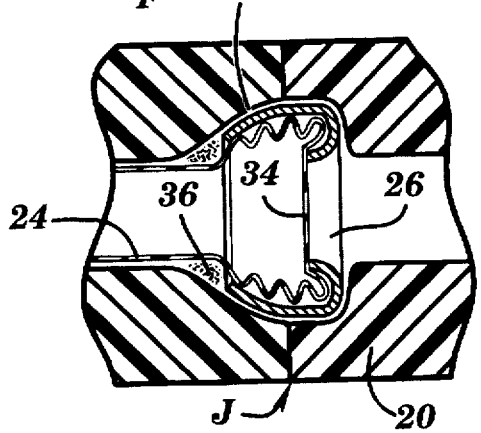
FIG. 2 is a detailed drawing of the shroud vault or repository taken at 2 of FIG. 1.
Figure 3:
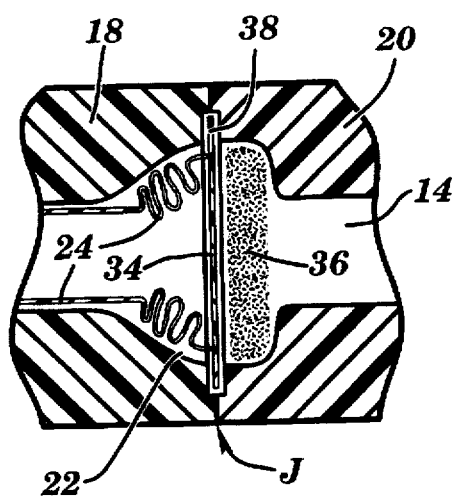
FIG. 3 is a rendering of FIG. 2 alternate shroud stowage.

In FIG. 2, a sectional detail of juncture J of distal portion 18 and proximal portion 20, reveals the chamber 22 in which a shroud holder 26 is disposed. The shroud 24 is seen extending to the left, in the detail, while its right side is both deposited into the holder and its closed end disposed over the central hole of the annular holder. The shroud right end forms a diaphram 34 which is pierced upon insertion therethrough of the catheter. Use of an optional diaphram at the proximal opening of the introducer 10 (not shown) ensures a portionwise or compartmental sterility of the overall apparatus. Sterile lubricant 36, common to the apparatus genre is afforded at several points, as shown herein, to enhance extraction of the shroud. FIG. 3 depicts a shroud 24 deposition in the chamber proper, but without the holder. In lieu of the holder, another form of annulus/toroid, a ring 38, serves as a frame for the closed end of the shroud. This end covers the hole in the ring forming the same type of diaphram 34 as seen in FIG. 2. In this alternate posturing of the shroud and ring 38 frame, lubricant 36 is positioned over the diaphram 34 and aids catheter movement beyond the juncture J and through the passage 14.

Figure 4:
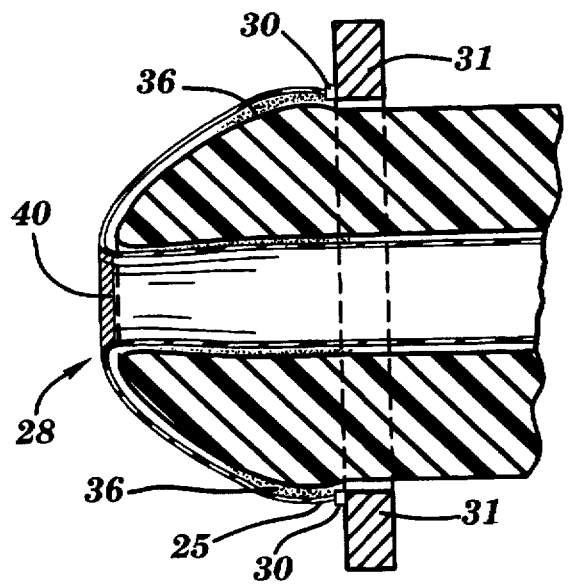
FIG. 4 is a sectional rendering of the distal portion of my invention.

The detail taken at 4 of FIG. 1 is presented as FIG. 4. Here, the distal opening shown in this sectional view is afforded a sterile lubricant plug 40 and the collar 30 is seen affixed to the hem 25 of the shroud. Projecting from the collar 30 are lobes 31. The latter feature is optional since the user of my invention can digitally manipulate the hem 25 via the collar 30; but lobes 31, or similar elements can enhance shroud extraction by their use as shown in FIG. 1. This duality of feature/function is further clarified in FIG. 5, which illustrates a shroud 24 adapted with a lobed 36 collar 30 at one end (open) and a ring 38-framed diaphram 34 at its other (closed) end. The diaphram 34 is scored 35, but not perforated, for ease of catheter passage. At a portion, 8—8, the shroud is afforded ribbing/corrugation 42, the function of which is described with FIG. 8. Final to FIG. 5 the detent(s) 33, projecting radially inward of the collar 30, are shown. This optional item is made to engage a longitudinal groove of the introducer body 12, as seen in FIG. 7 and discussed therewith. FIG. 6 is an abbreviated version of the FIG. 3 device; the distinction being that the shroud is stowed by overlapping. The diaphram (34) remains optional, the ring 38 affording either framing/mounting therefore, or simply an anchor for an open (hem) ended shroud.

A departure from the aforementioned repository/vault/chamber 22 is displayed in FIG. 7. Although generically the same regarding the shoud's disposition, no intermediate chamber of bulbous shape is used. Instead, the proximal portion 20 has an extention 44, but with a smaller outer diameter. A cylindrical chamber 22' is formed between proximal extention's 20/44 outer diameter (O.D.) and distal portion 18 inner diameter. The shroud is placed therein, being principally disposed about the 20/44 O.D. when manufactured and prior to final assembly. A singular collar detent 33 is shown disposed in groove 46 of the body 12. When lobes 31 are employed, use of the detent-in-groove 33,46 precludes twisting of the extracted shroud.

Finally, there is depicted in FIG. 8 the detail taken at 8—8 of FIG. 5. The ribs or corrugations 42 of the shroud 24 are integral with the shroud and arranged circumferentially transverse to its length. By their design, when extracted and repositioned outside the body 12, as depicted in phantom detail 50, they urge mucosa away from distal opening 28 and preclude seepage back toward it by capturing such liquids between the shroud 22 and the urethral walls. Also, their inherent relief serves to constrict the distal opening, thereby rendering unnecessary the use of distal plug 40.

Having presented the invention with alternates and adjuncts useful to medical practitioners, I commend its usage to them consistent with the hereinafter appended claims. Many options and differently formed assemblies may be created without departing from the claims or the spirit of the invention.

What is claimed is:

1. In a urethral catheter introduction device, having a bacterial avoidance means, for depositing a catheter antiseptically in the upper urethra above a normally contaminated lower portion thereof, a conduit with a distal end and a distal opening, a proximal end and a proximal opening, an interior passage communicating said distal opening with said proximal opening, said conduit receptive of a membrane-piercing catheter that is conductable though said passage, including an exterior collar member, and having a shroud member enclosed within the passage and deployable out of said distal opening, an improvement comprising:

said exterior collar member being translatable from a first distal position on the conduit towards a second proximal position; and said shroud member enclosed within the passage and deployable out of said distal opening to envelop the distal end of only the conduit, said shroud having an integrally-closed end forming a diaphamatic barrier means that is disposed crosswise inside the passage and is secured proximate the circumferential interior surface thereof, said shroud having an open end partially extracted from the passage and marginally attached about a perimetrical surface of the collar, whereby mechanical translation of the collar from the first distal position towards the second proximal position extractingly deploys more of the shroud about the conduit to the extent of said translation.

2. The improvement of claim 1 wherein the conduit further comprises a partial, hollow annulus to which the integrally closed end of said shroud is perimetrically attached and into which it is stowable.

3. The improvement of claim 1 in which the conduit is of a two part construction and joined between the distal end and the proximal end thereof, said shroud attached interiorly of the conduit proximate the joining of said conduit ends.

4. The improvement of claim 3 wherein the attachment of said shroud at the joining of the distal and the proximal ends secures the shroud circumferentially in the passage and effects said diaphramatic barrier means, perforable by said catheter, in the form of a cross-lumenal barrier within the conduit.

5. A catheter introducer comprising a tubular member having a distal opening and a lumen therethrough communicating with a proximal opening in a proximal end thereof, the tubular member including a slideable collar means that is mechanically translatable away from the distal opening, said introducer further comprising a membranous sleeve that is predominantly disposed within said lumen and having an integrally closed end which is dispose crosswise in the lumen to effect a perforable barrier, said sleeve partially exposed from out said lumen and joined peripherally to said collar means, whereby urging the collar means towards the proximal end extracts the lumen-disposed sleeve and effects an envelopment of the distal opening and an exterior distal portion of the introducer.

6. The introducer of claim 5 wherein said collar means is a tubular member-girdling means to which a hem of said sleeve is peripherally anchored.

7. The introducer of claim 6 wherein said distal opening exposing said sleeve is receptive of a lubricant plug.

8. The introducer of claim 6 wherein said collar means includes radial lobes.

9. The introducer of claim 6 wherein said collar means includes at least one guide detent.

10. The introducer of claim 5 wherein said sleeve includes circumferential corrugation means for engaging liquids.

11. In a collared introducer means for inserting a catheter into a urethra, while bypassing a known bacterial situs therewithin, said introducer means being a tubular means for conducting an elongate body therethrough and including a distal portion having a distal opening and a proximal portion, an improvement comprising, in combination:

an envelopment means, having a hem, for sleeving the distal portion of said tubular means, said envelopment means having therealong transverse circumferential ribbing, disposed within the tubular means and partially dispensed from thereout through said distal opening in said distal portion to convolvingly cover a part of the distal portion; and an engagement means disposed on the tubular means for capturing and transporting said hem of the envelopment means that is partially dispensed from out said distal opening towards the proximal portion of the tubular means, whereby transporting the hem as aforesaid establishes an envelope means barrier between urethral walls and the introducer means as the latter is manipulated into the urethra.

12. The improvement of claim 11 wherein the engagement means includes a collar means movably disposed about an exterior surface of the tubular means and fixedly attached to the hem of the envelopment means, said collar means facilitative of a proximal directional urging of the hem.

13. The improvement of claim 12 wherein said tubular means includes a longitudinal surface groove said collar means projects a detent radially inward to engage and slide through said longitadinal surface groove.

14. The improvement of claim 11 wherein the engagement means is a hem securement member that is manipulable by a person inserting the introducer means.

15. The improvement of claim 14 wherein said securement member includes at least one guide detent.

* * * * *